United States Patent
Fukushima

(10) Patent No.: US 10,125,154 B2
(45) Date of Patent: Nov. 13, 2018

(54) FLUORINE-CONTAINING ALKYLSILANE COMPOUND, AND METHOD FOR PRODUCING THE SAME

(71) Applicant: UNIMATEC CO., LTD., Tokyo (JP)

(72) Inventor: Takeshi Fukushima, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 15/512,444

(22) PCT Filed: Sep. 18, 2015

(86) PCT No.: PCT/JP2015/076699
§ 371 (c)(1),
(2) Date: Mar. 17, 2017

(87) PCT Pub. No.: WO2016/052262
PCT Pub. Date: Apr. 7, 2016

(65) Prior Publication Data
US 2017/0305938 A1    Oct. 26, 2017

(30) Foreign Application Priority Data
Sep. 30, 2014   (JP) ................................ 2014-200044

(51) Int. Cl.
| | | |
|---|---|---|
| C07F 7/08 | (2006.01) | |
| C07F 7/18 | (2006.01) | |
| C08G 65/00 | (2006.01) | |
| C03C 17/30 | (2006.01) | |
| C09D 183/08 | (2006.01) | |
| C08G 77/24 | (2006.01) | |
| C07B 61/00 | (2006.01) | |

(52) U.S. Cl.
CPC .............. *C07F 7/081* (2013.01); *C03C 17/30* (2013.01); *C07F 7/1804* (2013.01); *C08G 65/007* (2013.01); *C08G 77/24* (2013.01); *C09D 183/08* (2013.01); *C07B 61/00* (2013.01)

(58) Field of Classification Search
None
See application file for complete search history.

(56) References Cited

U.S. PATENT DOCUMENTS

| | | | |
|---|---|---|---|
| 4,820,674 A | 4/1989 | Shiozawa et al. | |
| 5,663,399 A | 9/1997 | Furukawa et al. | |
| 5,728,903 A | 3/1998 | Furukawa et al. | |
| 5,914,422 A | 6/1999 | Furukawa et al. | |
| 8,278,361 B2 | 10/2012 | Murata et al. | |
| 9,540,404 B2 | 1/2017 | Murotani et al. | |
| 2004/0186216 A1* | 9/2004 | Satoh ................... C03C 17/009 | |
| | | | 524/502 |
| 2010/0119848 A1 | 5/2010 | Yoshino | |
| 2010/0288971 A1 | 11/2010 | Murata et al. | |
| 2014/0302332 A1 | 10/2014 | Murotani et al. | |
| 2017/0291865 A1 | 10/2017 | Fukushima | |

FOREIGN PATENT DOCUMENTS

| | | |
|---|---|---|
| CN | 101646682 A | 2/2010 |
| EP | 3 202 756 A1 | 8/2017 |
| JP | 63-190648 | 8/1988 |
| JP | 02-178292 | 7/1990 |
| JP | 8-176307 | 7/1996 |
| JP | 2000-219875 A | 8/2000 |
| JP | 2009-137842 A | 6/2009 |
| JP | B 5292826 | 6/2013 |
| JP | 2014-40373 A | 3/2014 |
| WO | WO 2008/108438 A1 | 9/2008 |
| WO | WO 2012081524 A1 | 6/2012 |
| WO | WO 2013/121984 A1 | 8/2013 |

OTHER PUBLICATIONS

International Search Report from corresponding PCT application No. PCT/JP2015/076699 dated Dec. 15, 2015 (4 pgs).
International Preliminary Report on Patentability and Written Opinion from corresponding PCT application No. PCT/JP2015/076699 dated Apr. 13, 2017 ( 6 pages ).

* cited by examiner

*Primary Examiner* — Clinton A Brooks
*Assistant Examiner* — Kofi Adzamli
(74) *Attorney, Agent, or Firm* — Brinks Gilson & Lione

(57) ABSTRACT

A fluorine-containing alkylsilane compound represented by the general formula:

$$CF_3(CF_2)_n(CH_2CF_2)_a(CF_2CF_2)_b(CH_2)_3SiR_{3-d}X_d \quad \text{[I]}$$

wherein n is an integer of 0 to 5; a is 1 or 2; b is an integer of 0 to 3; R is a $C_1$-$C_3$ alkoxy group, a fluorine-containing alkoxy group, or an alkenyl group; X is halogen; and d is an integer of 0 to 3. The fluorine-containing alkylsilane compound is produced by reacting, in the presence of a transition metal catalyst, a polyfluoroalkyl allyl compound represented by the general formula:

$$CF_3(CF_2)_n(CH_2CF_2)_a(CF_2CF_2)_bCH_2CH=CH_2 \quad \text{[II]}$$

wherein n, a, and b are as defined above, with:
an alkoxysilane, or
a chlorosilane, followed by a reaction with lower alcohol or metal alkenyl. The production method gives a fluorine-containing alkylsilane compound that can remove free iodine derived from the raw material compound, before a hydrosilylation reaction is performed, without using a metal reagent having a high environmental load, and that also has excellent handling properties.

6 Claims, No Drawings

FLUORINE-CONTAINING ALKYLSILANE COMPOUND, AND METHOD FOR PRODUCING THE SAME

RELATED APPLICATION

This application is a 35 U.S.C. § 371 national phase filing of International Patent Application No. PCT/JP2015/076699, filed Sep. 18, 2015, which claims priority under 35 U.S.C. § 119 to Japanese Patent Application No. 2014-200044, filed Sep. 30, 2014, the entire disclosure of which is hereby expressly incorporated by reference.

TECHNICAL FIELD

The present invention relates to a fluorine-containing alkylsilane compound and a method for producing the same. More particularly, the present invention relates to a fluorine-containing alkylsilane compound having a high water contact angle, and a method for producing the fluorine-containing alkylsilane compound.

BACKGROUND ART

In general, compounds having a perfluoroalkyl group as a structural unit are known to improve surface modifying properties, water- and oil-repellency, mold releasability, antifouling properties, leveling properties, etc., of various substrates, such as fiber, metal, glass, rubber, and resin, by chemical treatment of the surface of each substrate.

Among such compounds, telomer compounds containing a perfluoroalkyl group having 8 to 12 carbon atoms are most likely to exhibit the above properties. Telomer compounds having 8 carbon atoms are preferably used.

However, it has been recently reported that perfluorooctanoic acid having 8 carbon atoms or perfluorocarboxylic acids having more than 8 carbon atoms have adverse effect on the environment, because they are hardly degradable and have high bioaccumulation potential, and they are thus suspected to be biotoxic. Among these compounds, those containing a perfluoroalkyl group having more than 8 carbon atoms are suggested to be possibly converted to perfluorooctanoic acid or perfluorocarboxylic acids having more than 8 carbon atoms by biodegradation or chemical degradation in the environment, and there is concern that it will become difficult to produce and use those compounds for the future. However, compounds containing a perfluoroalkyl group having 6 or less carbon atoms are said to have low bioaccumulation potential.

Fluorine-containing alkylsilane compounds containing a perfluoroalkyl group having 6 or less carbon atoms and having a high water contact angle are also known.

Patent Document 1 discloses a method for obtaining a fluorine-containing alkylsilane compound having terminal —CH$_2$CH$_2$Si(R$^1$)$_{3-n}$X$_n$ by reducing, with a reducing agent, a compound obtained by the addition reaction of R$^F$(CH$_2$CH$_2$)$_a$(CH$_2$CF$_2$)$_b$(CF$_2$CF$_2$)$_c$I with CH$_2$=CHSi(R$^1$)$_{3-n}$X$_n$.

In this method, however, iodine is desorbed in the final step, and there is thus a concern about coloring of the target compound with iodine. In addition, there is a problem that hydrogenated tributyltin and the like that have a high environmental load are used in the deiodination reaction. Moreover, it is described that a compound having a CH$_2$ group between a CF$_2$ group and a CF$_2$ group is weak under basic conditions, which means that the reaction conditions (synthesis root) are limited.

Patent Document 2 indicates that silane coupling agents having a biphenyl alkyl group Rf(C$_6$H$_4$—C$_6$H$_4$)CH$_2$CH$_2$CH$_2$Si(OCH)$_3$ are compounds having excellent heat resistance, durability, mold releasability, and antifouling properties, so that the contact angle of surfaces modified by these compounds are not reduced even after exposure to an atmosphere at a high temperature of 350° C. or more.

However, these compounds are solids at ordinary temperature because of the biphenyl skeleton in their molecules, and may be thus difficult to handle. Further, organic lithium, such as n-butyllithium, is used as a reaction reagent. This is a highly reactive and water-prohibiting regent. It is thus necessary to slowly drop such a reagent under low temperature conditions, since, for example, control of the reaction heat during the reaction becomes necessary. Thus, handling properties are poor, and the process used therein is not suitable for large-scale production.

A fluorine-containing alkylsilane compound having a bifunctional organosiloxane group is described in Patent Document 3.

PRIOR ART DOCUMENTS

Patent Documents

Patent Document 1: JP-A-2014-40373
Patent Document 2: WO 2008/108438 A1
Patent Document 3: JP-A-2009-137842
Patent Document 4: JP-B-5292826

OUTLINE OF THE INVENTION

Problem to be Solved by the Invention

An object of the present invention is to provide a fluorine-containing alkylsilane compound that can remove free iodine derived from the raw material compound, before a hydrosilylation reaction is performed, without using a metal reagent having a high environmental load, and that also has excellent handling properties; and to provide a method for producing the fluorine-containing alkylsilane compound.

Means for Solving the Problem

The present invention provides a fluorine-containing alkylsilane compound represented by the general formula:

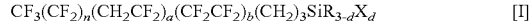

wherein n is an integer of 0 to 5; a is 1 or 2; b is an integer of 0 to 3; R is a C$_1$-C$_3$ alkoxy group, a fluorine-containing alkoxy group, or an alkenyl group; X is halogen; and d is an integer of 0 to 3.

The fluorine-containing alkylsilane compound is produced by reacting, in the presence of a transition metal catalyst, a polyfluoroalkyl allyl compound represented by the general formula:

wherein n, a, and b are as defined above, with:
an alkoxysilane,
or
a chlorosilane, followed by a reaction with lower alcohol or metal alkenyl.

Effect of the Invention

The present invention provides a fluorine-containing alkylsilane compound that can remove free iodine derived from the raw material compound, before a hydrosilylation reaction is performed, using a transition metal catalyst such as a Pt-based catalyst and that also has excellent handling properties.

The fluorine-containing alkylsilane compound of the present invention, to which a suitable hydrosilylating agent is added in the presence of a transition metal catalyst, can be chemically bonded to the surface of various substrates to thereby impart water- and oil-repellency, antifouling properties, etc., thereto. Accordingly, the fluorine-containing alkylsilane compound of the present invention can be used as an active component of a surface-treating agent.

EMBODIMENTS FOR CARRYING OUT THE INVENTION

The fluorine-containing alkylsilane compound of the present invention are produced through the following series of steps:
(1) A compound:

$$CF_3(CF_2)_n(CH_2CF_2)_a(CF_2CF_2)_bI \quad [IV]$$

is reacted with carboxylic acid allyl ester $R'COOCH_2CH=CH_2$.
(2) The resulting product:

$$CF_3(CF_2)_n(CH_2CF_2)_a(CF_2CF_2)_bCH_2CHICH_2OCOR' \quad [III]$$

is reacted with a transition metal.
(3) The resulting product:

$$CF_3(CF_2)_n(CH_2CF_2)_a(CF_2CF_2)_bCH_2CH=CH_2 \quad [II]$$

is reacted with alkoxysilane,
or reacted with chlorosilane followed by a reaction with $C_1$-$C_3$ lower alcohol or metal alkenyl,
thereby obtaining the following compound:

$$CF_3(CF_2)_n(CH_2CF_2)_a(CF_2CF_2)_b(CH_2)_3SiR_{3-d}X_d \quad [I].$$

Examples of $C_1$-$C_3$ lower alcohol usable herein include fluorine-free alcohols, such as methanol, ethanol, propanol, and isopropanol; and fluorine-containing alcohols, such as trifluoroethanol, tetrafluoropropanol, and hexafluoroisopropanol. Moreover, examples of metal alkenyl include allyl magnesium chloride, allyl magnesium bromide, and the like.

The polyfluoroalkyl iodide [IV] used as a raw material compound in step (1) above is a known compound, and disclosed, for example, in Patent Document 4.

Specific examples of the polyfluoroalkyl iodide used include the following compounds:

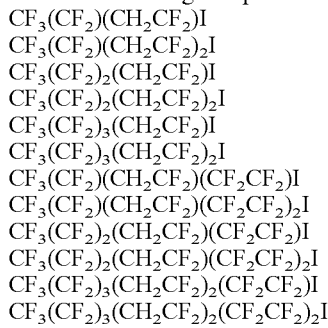

$CF_3(CF_2)(CH_2CF_2)I$
$CF_3(CF_2)(CH_2CF_2)_2I$
$CF_3(CF_2)_2(CH_2CF_2)I$
$CF_3(CF_2)_2(CH_2CF_2)_2I$
$CF_3(CF_2)_3(CH_2CF_2)I$
$CF_3(CF_2)_3(CH_2CF_2)_2I$
$CF_3(CF_2)(CH_2CF_2)(CF_2CF_2)I$
$CF_3(CF_2)(CH_2CF_2)(CF_2CF_2)_2I$
$CF_3(CF_2)_2(CH_2CF_2)(CF_2CF_2)I$
$CF_3(CF_2)_2(CH_2CF_2)(CF_2CF_2)_2I$
$CF_3(CF_2)_3(CH_2CF_2)_2(CF_2CF_2)I$
$CF_3(CF_2)_3(CH_2CF_2)_2(CF_2CF_2)_2I$

As a slightly excess mole number of carboxylic acid allyl ester $R'COOCH_2CH=CH_2$ to be reacted with such a polyfluoroalkyl iodide, compounds, in which R' has a $C_1$-$C_3$ alkyl group, preferably allyl acetate are used. This reaction is performed as a radical addition reaction at a temperature of about 70 to 120° C. in the presence of a radical initiator in an amount of about 0.001 to 1.0 mol % based on the polyfluoroalkyl iodide. Examples of the radical initiator include peroxydicarbonates, such as di-n-propyl peroxydicarbonate, diisopropyl peroxydicarbonate, di(4-tert-butylcyclohexyl) peroxydicarbonate, di(2-ethoxyethyl) peroxydicarbonate, di(2-ethoxyhexyl) peroxydicarbonate, di(3-methoxybutyl) peroxydicarbonate, and di-sec-butyl peroxydicarbonate.

The resulting carboxylic acid allyl adduct [III] is reacted with a transition metal, for example, a simple metal such as Zn, Mg, Mn, Cu or a reagent thereof, preferably simple Zn, as the reduction of iodine and olefination reaction. The carboxylic acid allyl adduct and the transition metal are each used together with a solvent, such as methanol and ethanol. Moreover, the transition metal is used in a slightly excess molar ratio based on the carboxylic acid allyl adduct.

The resulting polyfluoroalkyl allyl compound [II]:

$$CF_3(CF_2)_n(CH_2CF_2)_a(CF_2CF_2)_bCH_2CH=CH_2$$

is reacted with an alkoxysilane to thereby yield the target compound:

$$CF_3(CF_2)_n(CH_2CF_2)_a(CF_2CF_2)_b(CH_2)_3SiR_{3-d}X_d \quad [I].$$

Examples of alkoxysilane include trimethoxysilane, triethoxysilane, tripropoxysilane, and the like, having a $C_1$-$C_3$ lower alkoxy group. The alkoxysilane is used in slightly excess molar ratio based on the terminal allyl compound.

The reaction is performed at a reaction temperature of about 25 to 100° C. in the presence of a transition metal catalyst. Examples of transition metal catalysts, preferably Pt-based or Rh-based catalysts, include chloroplatinic acid $H_2PtCl_{16}\cdot 6H_2O$, Karstedt's catalyst $Pt.CH_2=CHSiMe_2OMe_2OSiCH=CH_2$, Wilkinson's catalysts $RhCl[P(C_6H_5)_3]_3$, $RhH[P(C_6H_5)_3]_4$, and the like. The catalyst is used in an amount of about 0.001 to 10 mol % based on the polyfluoroalkyl allyl compound.

The polyfluoroalkylallyl compound [II] can also be reacted with slightly excess molar ratio of chlorosilane, followed by a reaction with $C_1$-$C_3$ lower alcohol or metal alkenyl, thereby obtaining the target compound. The reaction with chlorosilane is performed using a transition metal catalyst as mentioned above at a ratio of about 0.001 to 10 mol % based on the polyfluoroalkyl allyl compound at a reaction temperature of about 25 to 100° C., and after imparting —$SiCl_3$ to a terminal group, the resultant is reacted with a $C_1$-$C_3$ lower alcohol or metal alkenyl at a reaction temperature of about 25 to 120° C. When fluorine-free alcohol is used as the lower alcohol, R is an alkoxy group. When fluorine-containing alcohol is used as the lower alcohol, R is a fluorine-containing alkoxy group. In this case, less than 3 equivalents of lower alcohol or metal alkenyl can be reacted with the terminal —$SiCl_3$ group, thereby allowing halogen to remain in the terminal group.

The obtained fluorine-containing alkylsilane compound has a high water contact angle, which indicates a low surface free energy, and therefore indicates high mold releasability, and high antifouling properties.

EXAMPLES

The following describes the present invention with reference to Examples.

Reference Example 1

A 1000-ml three-necked flask was equipped with a dropping funnel and a Dimroth condenser in the presence of inert nitrogen gas. 400 g (0.66 mol) of polyfluoroalkyl iodide $CF_3(CF_2)_3(CH_2CF_2)(CF_2CF_2)_2I$ was charged in the three-necked flask, while 74.0 ml (0.69 mol) of allyl acetate $CH_2=CHCH_2OCOCH_3$ and 2.61 g (6.5 mmol) of a radical initiator P-16 [di(tert-butylcyclohexyl) peroxydicarbonate] were placed in the dropping funnel, respectively, and the content of the three-necked flask was stirred. When the temperature reached 90° C., droppings from the dropping funnel was started to initiate reaction. Heat generation was weak in the latter half of the reaction; therefore, 0.09 g of P-16 was added to allow the reaction to continue.

Two hours later after completion of the heat generation, the temperature was cooled to room temperature. The reaction mixture was analyzed by NMR and gas chromatography to confirm the structure and conversion of the reaction product. The conversion of the target product was 87%. Unreacted raw material compounds were removed by vacuum distillation, thereby obtaining 391 g (95% GC, yield: 84%) of light yellow solid allyl acetate adduct.

$CF_3CF_2CF_2CF_2CH_2CF_2CF_2CF_2CF_2CH_2CHICH_2OCOCH_3$ $^{19}$F-NMR (d-acetone, 282.65 Hz):
−80.2: $C\underline{F}_3CF_2CF_2CF_2CH_2CF_2CF_2CF_2CF_2CF_2CH_2$—
−110.3: $CF_3CF_2CF_2C\underline{F}_2CH_2C\underline{F}_2CF_2CF_2CF_2CF_2CH_2$—
−112.2: $CF_3CF_2CF_2CF_2CH_2CF_2CF_2CF_2CF_2C\underline{F}_2CH_2$—
−120.2: $CF_3CF_2CF_2CF_2CH_2C\underline{F}_2CF_2CF_2CF_2CF_2CH_2$—
−121.9: $CF_3CF_2CF_2CF_2CH_2CF_2C\underline{F}_2CF_2CF_2CF_2CH_2$—
−122.5: $CF_3C\underline{F}_2CF_2CF_2CH_2CF_2CF_2CF_2C\underline{F}_2CF_2CH_2$—
−124.9: $CF_3C\underline{F}_2CF_2CF_2CH_2CF_2CF_2CF_2CF_2CF_2CH_2$—

Reference Example 2

A 500-ml three-necked flask was equipped with a dropping funnel and a Dimroth condenser in the presence of inert nitrogen gas. 180 ml of methanol and 20.1 g (0.33 mol) of Zn were placed in the flask, while 200 g (0.28 mol) of the allyl acetate adduct obtained in Reference Example 1 and 20 ml of methanol were placed in the dropping funnel, respectively, and the content of the three-necked flask was stirred. When reflux started to occur, droppings from the dropping funnel was started to initiate reaction. After dropping, the resulting mixture was stirred for 2 hours, and then cooled to room temperature to stop the reaction.

Since the phase separation of the reaction mixture was unclear, an attempt was made to cause liquid separation by distilling off the methanol; however, an emulsion was formed. Accordingly, the precipitate was filtered, followed by liquid separation again and drying, thereby obtaining 123.7 g (92% GC, yield: 77%) of the target compound, i.e., a transparent liquid terminal allyl compound. In this reaction, it was confirmed that the reaction proceeded with good reproducibility, irrespective of the purity of the starting material. Next, vacuum distillation was performed to increase the purity to 97% GC.

$CF_3CF_2CF_2CF_2CH_2CF_2CF_2CF_2CF_2CH_2CH=CH_2$ $^1$H-NMR (d-acetone, 300.4 Hz):
δ5.9-5.7: —$CF_2CH_2C\underline{H}=CH_2$(m)
5.4: —$CF_2CH_2C\underline{H}=CH_2$(m)
3.6: —$CF_2C\underline{H}_2CF_2$-(quin)
3.0: —$CF_2C\underline{H}_2CH=CH_2$(dt)

$^{19}$F-NMR (d-acetone, 282.65 Hz):
−80.2: $C\underline{F}_3CF_2CF_2CF_2CH_2CF_2CF_2CF_2CF_2CF_2CH_2$—
−110.2: $CF_3CF_2CF_2C\underline{F}_2CH_2C\underline{F}_2CF_2CF_2CF_2CF_2CH_2$—
−111.9: $CF_3CF_2CF_2CF_2CH_2CF_2CF_2CF_2CF_2C\underline{F}_2CH_2$—
−120.3: $CF_3CF_2CF_2CF_2CH_2CF_2C\underline{F}_2CF_2CF_2CF_2CH_2$—
−121.9: $CF_3CF_2CF_2CF_2CH_2CF_2CF_2C\underline{F}_2CF_2CF_2CH_2$—
−122.1: $CF_3CF_2CF_2CF_2CH_2CF_2CF_2CF_2C\underline{F}_2CF_2CH_2$—
−122.5: $CF_3CF_2C\underline{F}_2CF_2CH_2CF_2CF_2CF_2CF_2CF_2CH_2$—
−124.9: $CF_3C\underline{F}_2CF_2CF_2CH_2CF_2CF_2CF_2CF_2CF_2CH_2$—

Example 1

A 100-ml three-necked flask was equipped with a septum and a Dimroth condenser in the presence of inert nitrogen gas. 20.0 g (0.04 mol) of the terminal allyl compound obtained in Reference Example 2 and 5.8 ml (0.05 mol) of triethoxysilane were placed in the three-necked flask. The content of the three-necked flask was stirred, and the temperature was increased to 80° C. After the temperature increase, 20 mg (0.05 mol % based on the terminal allyl compound) of chloroplatinic acid $H_2PtCl_6·6H_2O$ was added to initiate reaction. After stirring for the whole day and night, the reaction mixture was cooled to room temperature to stop the reaction.

The reaction mixture was subjected to vacuum distillation, thereby obtaining 10.7 g (yield: 42%) of the target compound, i.e., a transparent liquid terminal triethoxysilyl-propyl derivative.

$CF_3CF_2CF_2CF_2CH_2CF_2CF_2CF_2CF_2CH_2CH_2CH_2Si(OCH_2CH_3)_3$ $^1$H-NMR (CDCl$_3$, 300.4 Hz):
δ3.83: —$Si(OC\underline{H}_2CH_3)_3$(q)
2.92: —$CF_2C\underline{H}_2CF_2$-(quin)
2.13: —$C\underline{H}_2CH_2CH_2$-(tt)
1.75: —$CH_2C\underline{H}_2CH_2$-(m)
1.21: —$Si(OCH_2C\underline{H}_3)_3$(t)
0.70: —$CH_2CH_2C\underline{H}_2$-(t)

$^{19}$F-NMR (CDCl$_3$, 282.65 Hz):
−82.2: $C\underline{F}_3CF_2CF_2CF_2CH_2CF_2CF_2CF_2CF_2CF_2CH_2$—
−113.2: $CF_3CF_2CF_2C\underline{F}_2CH_2C\underline{F}_2CF_2CF_2CF_2CF_2CH_2$—
−115.6: $CF_3CF_2CF_2CF_2CH_2CF_2CF_2CF_2CF_2C\underline{F}_2CH_2$—
−122.5: $CF_3CF_2CF_2CF_2CH_2CF_2C\underline{F}_2CF_2CF_2CF_2CH_2$—
−124.0 to −126.0: $CF_3CF_2C\underline{F}_2CF_2C\underline{H}_2CF_2CF_2C\underline{F}_2CF_2CF_2CH_2$—
−127.0: $CF_3C\underline{F}_2CF_2CF_2CH_2CF_2CF_2CF_2CF_2CF_2CH_2$—

Example 2

A 100-ml three-necked flask was equipped with a septum and a Dimroth condenser in the presence of inert nitrogen gas. 20.0 g (0.04 mol) of the terminal allyl compound obtained in Reference Example 2 and 4.8 ml (0.05 mmol) of trichlorosilane SiHCl$_3$ were placed in the three-necked flask. The content of the three-necked flask was stirred, and the temperature was increased to 40° C. After the temperature increase, 14.5 mg (0.1 mol % based on the terminal allyl compound) of Karstedt's catalyst (Pt.CH$_2$=CHSiMe$_2$OMe$_2$SiCH=CH$_2$) was added to initiate the reaction. The oil bath temperature was gradually increased. When the temperature reached 100° C., the temperature was maintained at a constant, and stirring was performed for the whole day and night. After the disappearance of raw materials was confirmed by NMR, the reaction was stopped by cooling the reaction mixture to room temperature.

Next, without purifying a terminal trichlorosilyl product produced by this reaction, 3.7 ml (0.05 mol) of methyl orthoformate CH(OCH$_3$)$_3$ was added thereto, and the mixture was heated to 40° C. After confirming that the reaction solution became homogeneous, 5.6 ml (0.15 mol) of methanol was added, and the mixture was stirred for 1 hour, followed by distilling off of low-boiling components and vacuum distillation, thereby obtaining 10.10 g (yield: 41%) of the target compound, i.e., a transparent liquid terminal trimethoxysilylpropyl derivative.

$CF_3CF_2CF_2CF_2CH_2CF_2CF_2CF_2CF_2CH_2CH_2CH_2Si(OCH_3)_3$ $^1$H-NMR (CDCl$_3$, 300.4 Hz):
δ3.58:—Si(OC$\underline{H}_3$)$_3$(s)
2.92:—CF$_2$C$\underline{H}_2$CF$_2$-(quin)
2.12: —C$\underline{H}_2$C$\underline{H}_2$CH$_2$-(tt)
1.74: —C$\underline{H}_2$C$\underline{H}_2$CH$_2$-(m)
0.72: —CH$_2$C$\underline{H}_2$C$\underline{H}_2$-(t)

$^{19}$F-NMR (CDCl$_3$, 282.65 Hz):
−82.1:C$\underline{F}_3$CF$_2$CF$_2$CF$_2$CH$_2$CF$_2$CF$_2$CF$_2$CF$_2$CH$_2$—
−113.2:C$\overline{F}_3$CF$_2$CF$_2$C$\underline{F}_2$CH$_2$C$\underline{F}_2$CF$_2$CF$_2$CF$_2$CH$_2$—
−115.6:CF$_3$CF$_2$CF$_2$C$\overline{F}_2$CH$_2$CF$_2$CF$_2$CF$_2$CF$_2$C$\underline{F}_2$CH$_2$—
−122.5:CF$_3$CF$_2$CF$_2$CF$_2$CH$_2$CF$_2$C$\underline{F}_2$CF$_2$CF$_2$C$\underline{F}_2$CH$_2$—
−124.0 to −126.0:CF$_3$CF$_2$C$\underline{F}_2$CF$_2$C$\overline{H}_2$CF$_2$CF$_2$C$\underline{F}_2$C$\underline{F}_2$CF$_2$CH$_2$—
−127.0:CF$_3$C$\underline{F}_2$CF$_2$CF$_2$CH$_2$CF$_2$CF$_2$CF$_2$CF$_2$CH$_2$—

Comparative Example

In Example 2, 30 g (0.08 mol) of $C_6F_{13}CH_2CH=CH_2$ was used in place of the terminal allyl compound, and the amount of the Karstedt's catalyst was changed to 31.6 g (0.1 mol % based on the terminal allyl compound), the amount of trichlorosilane was changed to 10.1 ml (0.105 mol), the amount of methanol was changed to 12 ml (0.30 mol), the amount of methyl orthoformate was changed to 7.7 ml (0.1 mol), and the temperature to react with trichlorosilane was changed to 60° C., respectively. As a result, 31.66 g (yield: 79%) of a transparent liquid terminal trimethoxysilylpropyl derivative was obtained.

$CF_3CF_2CF_2CF_2CF_2CF_2CH_2CH_2CH_2$—$Si(OCH_3)_3$ $^1$H-NMR (CDCl$_3$, 300.4 Hz):
δ3.63:—Si(OC$\underline{H}_3$)$_3$(s)
2.10: —C$\underline{H}_2$CH$_2$CH$_2$-(quin)
1.81:—CH$_2$C$\underline{H}_2$-(m)
1.74: —CH$_2$C$\underline{H}_2$C$\underline{H}_2$-(t)

$^{19}$F-NMR (CDCl$_3$, 282.65 Hz):
—82.0:C$\underline{F}_3$CF$_2$CF$_2$CF$_2$CF$_2$CF$_2$CH$_2$—
—115.6:CF$_3$CF$_2$CF$_2$CF$_2$CF$_2$C$\underline{F}_2$CH$_2$—
—123.1:CF$_3$CF$_2$CF$_2$CF$_2$C$\underline{F}_2$CF$_2$CH$_2$—
—124.0:CF$_3$CF$_2$C$\underline{F}_2$CF$_2$CF$_2$CF$_2$CH$_2$—
—124.8:CF$_3$CF$_2$C$\underline{F}_2$C$\underline{F}_2$CF$_2$CF$_2$CH$_2$—
—127.3:CF$_3$C$\underline{F}_2$CF$_2$CF$_2$CF$_2$CF$_2$CH$_2$—

Reference Example 3

Substrate: Matsunami Glass (Preclean water edge polishing S7213)
Solution: 100 g of Vertrel, 0.1 g of sample, 40 mg of 0.05 M hydrochloric acid, and 5 ml of methanol
Coating conditions: spin coating, 0.5 g, 1000 rpm, 30 seconds
Drying conditions: 23° C., 50% RH The following table shows the results of the measurement of the contact angle of each sample under the above conditions.

TABLE

| No. | Sample | Contact angle (°) | |
|---|---|---|---|
| | | H$_2$O | Hexadecane |
| 1 | Ex. 1 | 108 | 69 |
| 2 | Ex. 2 | 108 | 69 |
| 3 | C$_6$F$_{13}$CH$_2$CH$_2$Si(OEt)$_3$ | 106 | 63 |
| 4 | Comp. Ex. | 106 | 73 |
| 5 | C$_8$F$_{17}$CH$_2$CH$_2$Si(OEt)$_3$ | 109 | 69 |

The invention claimed is:

1. A fluorine-containing alkylsilane compound represented by the general formula:

$$CF_3(CF_2)_n(CH_2CF_2)_a(CF_2CF_2)_b(CH_2)_3SiR_{3-d}X_d \qquad [I]$$

wherein n is an integer of 0 to 5; a is 1 or 2; b is an integer of 0 to 3; R is a C$_1$-C$_3$ alkoxy group, a fluorine-containing alkoxy group, or an alkenyl group; X is halogen; and
d is an integer of 0 to 3.

2. A method for producing the fluorine-containing alkylsilane compound according to claim 1, the method comprising reacting, in the presence of a transition metal catalyst, a polyfluoroalkyl allyl compound represented by the general formula:

$$CF_3(CF_2)_n(CH_2CF_2)_a(CF_2CF_2)_bCH_2CH=CH_2 \qquad [II]$$

wherein n is an integer of 0 to 5, a is 1 or 2, and b is an integer of 0 to 3, with an alkoxysilane having a C$_1$-C$_3$ lower alkyl group.

3. The method for producing the fluorine-containing alkylsilane compound according to claim 2, wherein the transition metal catalyst is a Pt-based or Rh-based catalyst.

4. A method for producing the fluorine-containing alkylsilane compound according to claim 1, the method comprising reacting, in the presence of a transition metal catalyst, a polyfluoroalkyl allyl compound represented by the general formula:

$$CF_3(CF_2)_n(CH_2CF_2)_a(CF_2CF_2)_bCH_2CH=CH_2 \qquad [II]$$

wherein n is an integer of 0 to 5, a is 1 or 2, and b is an integer of 0 to 3, with a chlorosilane, followed by a reacting with a C$_1$-C$_3$ lower alcohol or metal alkenyl.

5. The method for producing the fluorine-containing alkylsilane compound according to claim 4, wherein the transition metal catalyst is a Pt-based or Rh-based catalyst.

6. A surface-treating agent comprising the fluorine-containing alkylsilane compound according to claim 1 as an active ingredient.

* * * * *